United States Patent
Kim

(10) Patent No.: US 6,776,786 B2
(45) Date of Patent: Aug. 17, 2004

(54) EARPICK

(75) Inventor: Yongup Kim, Seoul (KR)

(73) Assignee: Soo-Hee Kim, Seoul (KR)

( * ) Notice: Subject to any disclaimer, the term of this patent is extended or adjusted under 35 U.S.C. 154(b) by 223 days.

(21) Appl. No.: 10/107,134

(22) Filed: Mar. 28, 2002

(65) Prior Publication Data

US 2003/0163150 A1 Aug. 28, 2003

(30) Foreign Application Priority Data

Feb. 26, 2002 (KR) .................................... 2002-0005631

(51) Int. Cl.[7] .............................................. A61F 11/00
(52) U.S. Cl. ...................................................... 606/162
(58) Field of Search ................................ 606/160, 161, 606/162, 114

(56) References Cited

U.S. PATENT DOCUMENTS

| | | | | |
|---|---|---|---|---|
| 928,011 A | * | 7/1909 | Whitlock | 606/160 |
| 2,617,420 A | * | 11/1952 | Jozefczyk | 606/162 |
| 5,902,314 A | * | 5/1999 | Koch | 606/162 |

* cited by examiner

*Primary Examiner*—Kevin T. Truong
(74) *Attorney, Agent, or Firm*—Greenblum & Bernstein, P.L.C.

(57) ABSTRACT

An earpick includes a handle; a support bar movably coupled to the handle; and an earwax cleaning portion coupled to the support bar, wherein when the earpick deeply enter and contacts an inner wall of an auditory canal, the support bar moves into the hanndle. The earwax cleaning portion has a ring shaped cross-section.

10 Claims, 5 Drawing Sheets

EARPICK

BACKGROUND OF THE INVENTION

1. Field of the invention

The present invention relates to an ear-pick for cleaning an earwax.

2. Description of Related Art

An earpick is used to clean an earwax generated in an earhole of a human body in order to keep a clean body.

A conventional earpick has a scoop-shaped portion which substantially clean an earwax. A user makes the earpick contact an inner wall of an auditory canal in order to clean the earwax, and thus there is a possibility of hurting the inner wall of the auditory canal.

In particular, in case of a patient or the old and the weak, due to an unstable hand movement, their ear may get hurt. Further, during a cleaning of the earwax, a user cannot ascertain an accurate depth that the earpick enters into the auditory carnal. In certain cases, even the ear drum can be hurt.

SUMMARY OF THE INVENTION

To overcome the problems described above, it is an object of the present invention to provide an earpick which can clean an earwax easily and safely.

In order to achieve the above object, the preferred embodiments of the present invention provide an earpick, comprising: a handle; a support bar movably coupled to the handle; and an earwax cleaning portion coupled to the support bar, wherein when the earpick deeply enter and contacts an inner wall of an auditory canal, the support bar moves into the hanndle.

The earwax cleaning portion has a ring shaped cross-section such as an elliptic cross section, a circular cross section, or a letter "C" shaped cross section.

The earpick further includes an elastic plate folded in a laid letter "U" form. The elastic plate has a through hole and concave grooves opposite to each other, so that the support bar passes through the through hole and is pressed by the concave grooves. A portion of the support bar pressed by the concave grooves has a plurality of concave-convex portions.

One end of the support bar is flat, so that when the support bar is pulled out, the flat end prevents the support bar from being separated from the handle.

The handle includes a fron handle and a rear handle screw-coupled to each other. The rear handle has at least one flat portion formed in the same direction of the earwax cleaning portion, whereby the handle is easy to grasp.

BRIEF DESCRIPTION OF THE DRAWINGS

For a more complete understanding of the present invention and the advantages thereof, reference is now made to the following descriptions taken in conjunction with the accompanying drawings, in which like reference numerals denote like parts, and in which.

DETAILED DESCRIPTION OF PREFFERED EMBODIMENTS

Reference will now be made in detail to preferred embodiments of the present invention, example of which is illustrated in the accompanying drawings.

Figure 1:
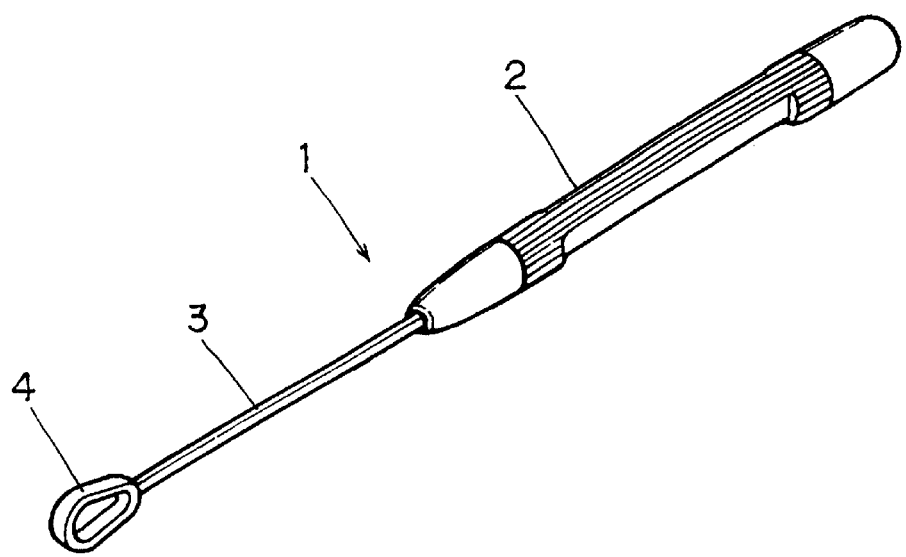
FIGS. 1 to 3 illustrate an earpick according to one embodiment of the present invention.
Figure 2:
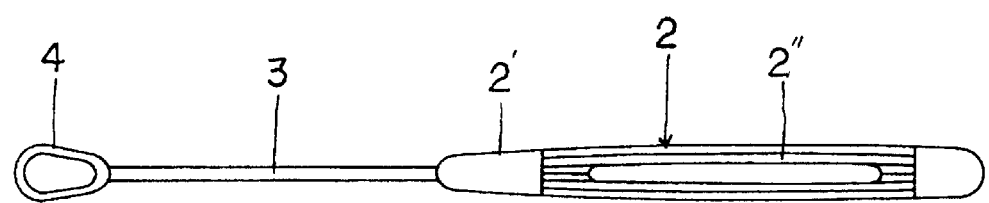
Figure 3:
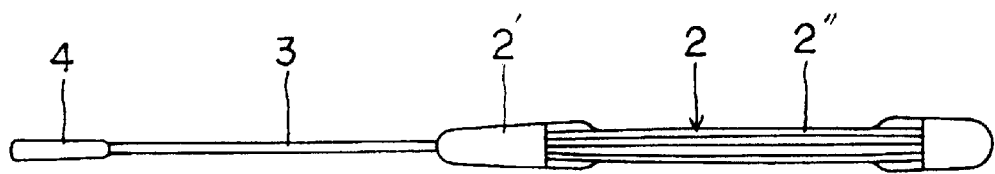

FIGS. 1 to 3 show an earpick according to one embodiment of the present invention.

The earpick includes 1 includes a handle 2, a support bar 3, and an earwax cleaning portion 4.

The handle 2 has a hollow tube shape, and includes a front handle 2' and a rear handle 2" which are screw-coupled to each other. Flat portions are formed on the rear handle 2" in the same direction as the earwax cleaning portion 4 to easily to grasp.

The support bar 3 is preferably made of a flexible material, and is movably coupled to the handle 2. That is, when the earpick 1 deeply enters the auditory canal and pricks an inner wall of the auditory canal, the support bar 3 moves into an inner space 5 of the handle 2. Therefore, it is possible to prevent the inner wall of the auditory canal from being hurt.

Figure 10:
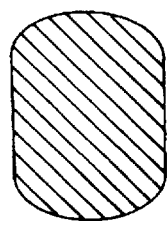
FIG. 10 illustrates a cross section of a support bar of the earpick according to the present invention.

The support bar 3 can have various cross sections such as a circular cross section, an elliptic cross section (see FIG. 10), a triangular cross section, or a rectangular cross section. In case of the support bar 3 having a cross section other a circular cross section, a rotation of the support bar 3 is prevented, whereby an earwax can be cleaned stably.

Figure 6:
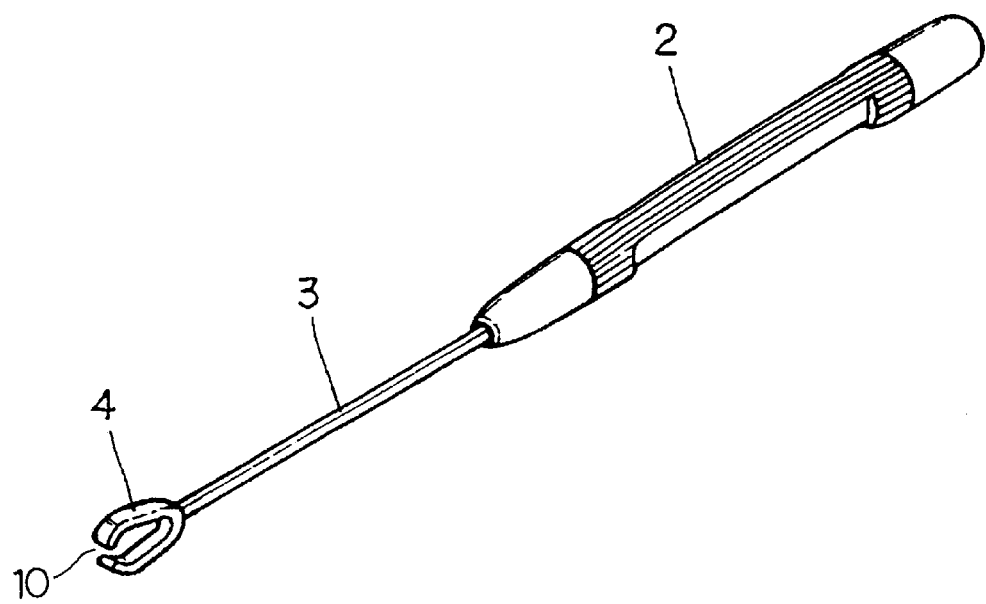
FIGS. 6 and 7 are perspective views illustrating modifications of the earpick according to the present invention.
Figure 7:
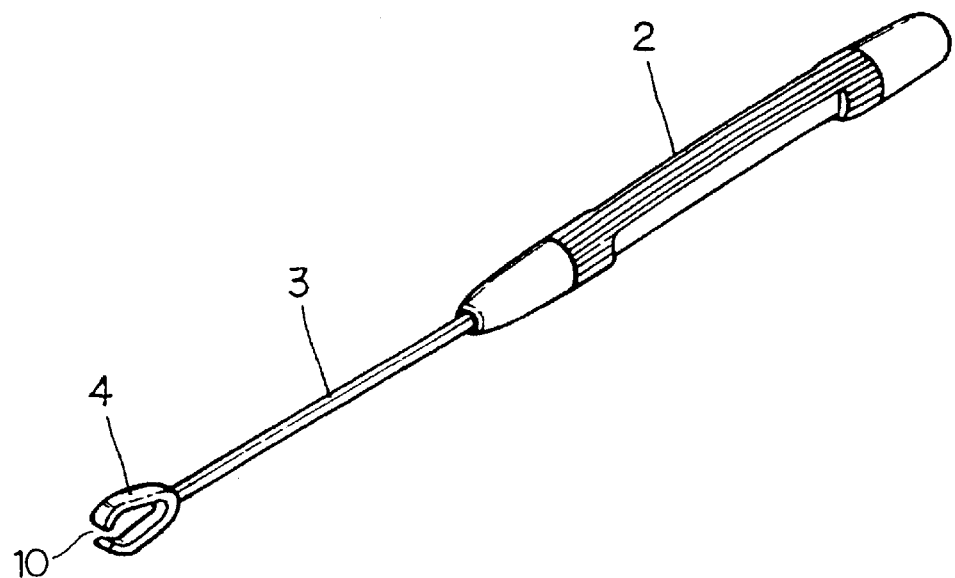

The earwax cleaning portion 4 is coupled to one end of the support bar 3, and has a ring shape having an elliptic cross-section. The earwax cleaning portion 4 can have a ring shape having a circular cross-section as shown in FIG. 6. Or, the earwax cleaning portion 4 can have a letter "C" shape. In this case, an open portion 10 is formed in the earwax cleaning portion 4.

Figure 4:
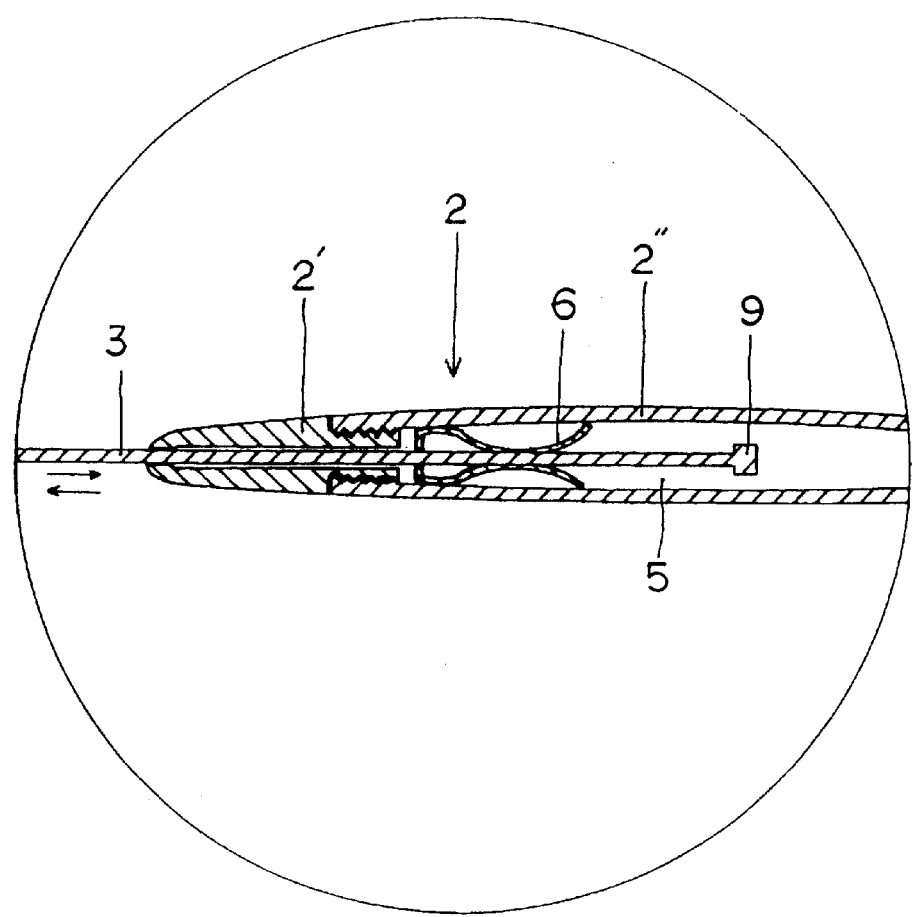
FIG. 4 is an enlarged cross-sectional view of the earpick according to the present invention.
Figure 5:
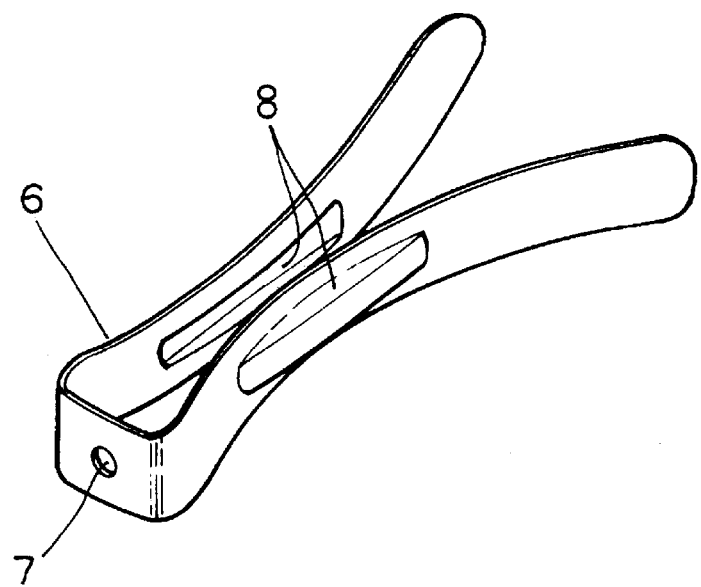
FIG. 5 is a perspective view of an elastic plate of the earpick according to the present invention.

Referring to FIGS. 4 and 5, an elastic plate 6 which is folded in laid letter "U" form is arranged in the inner space 5 of the handle 2. The elastic plate 6 includes a through hole 7 and concave grooves 8 opposite to each other, so that the support bar 3 passes through the through hole 7 and is pressed by the concave grooves 8.

The other end 9 of the support bar 3 is flat. When the support bar 3 is pulled out, the flat end 9 prevents the support bar 3 from being separated from the handle 2. Even though not shown, a portion of the support bar 3 interposed between the two concave grooves 8 of the elastic plate 6 has a plurality of concave-convex portions. Therefore, since the elastic plate 6 slightly presses the support bar 2, the support bar 3 moves into or moves out smoothly and roughly.

Meanwhile, the concave-convex portions of the support bar 3 can be formed in handle direction so that the support bar 3 move smoothly when it get into the inner space 5 but moves roughly when it get out of the inner space 5.

Consequently, when the earpick 1 deeply enters the auditory canal and pricks the inner wall of the auditory canal, the support bar 3 smoothly moves into an inner space 5 of the handle 2. Therefore, it is prevent to hurt the inner wall of the auditory canal or the ear drum.

Figure 8:
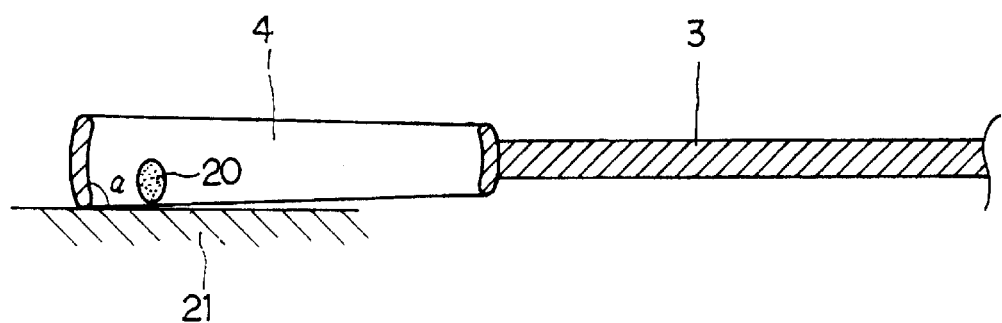
FIG. 8 is a cross-sectional view illustrating a method of cleaning an earwax using the earpick according to the present invention.
Figure 9:
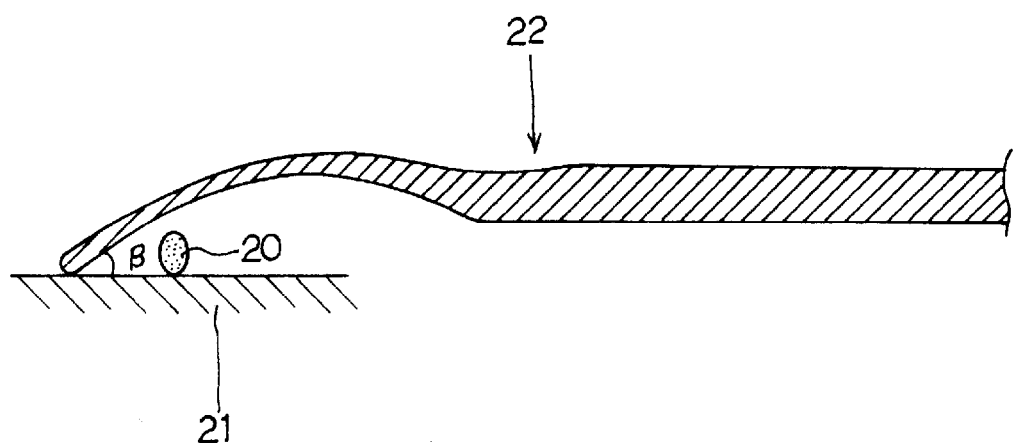
FIG. 9 is a cross-sectional view illustrating a method of cleaning an earwax using a conventional earpick.

FIG. 8 is a cross-sectional view illustrating a method of cleaning an earwax using the earpick according to the present invention. FIG. 9 is a cross-sectional view illustrating a method of cleaning an earwax using a conventional earpick.

Referring to FIGS. 8 and 9, the conventional earpick 22 is inefficient in cleaning the earwax 20 because an angle β formed by the earwax cleaning portion and the inner wall 21 of the auditory canal is a complementary angle, whereas the inventive earpick 1 is very efficient in cleaning an earwax because an angle α formed by the earwax cleaning portion 4 and the inner wall 21 of the auditory canal is close to 90°.

As described herein before, the earpick according to the present invention can clean the earwax easily and safely.

While the invention has been particularly shown and described with reference to preferred embodiments thereof, it will be understood by those skilled in the art that the foregoing and other changes in form and details may be made therein without departing from the spirit and scope of the invention.

What is claimed is:

1. An earpick, comprising:

a handle;

a support bar movably coupled to the handle;

an earwax cleaning portion coupled to the support bar;

an elastic plate that engages and presses against the support bar as the support bar moves into and out of the handle, wherein when the earpick deeply enters and contacts an inner wall of an auditory canal, the support bar moves into the hanndle.

2. The earpick of claim 1, wherein the earwax cleaning portion has a ring shaped cross-section.

3. The earpick of claim 2, wherein the earwax cleaning portion has an elliptic cross section, a circular cross section, or a letter "C" shaped cross section.

4. An earpick, comprising:

a handle;

a support bar movably coupled to the handle;

an earwax cleaning portion coupled to the support bar; and an elastic plate folded in a laid letter "U" form, the elastic plate having a through hole and concave grooves opposite to each other, wherein the support bar passes through the through hole and is pressed by the concave grooves, and when the earpick deeply enters and contacts an inner wall of an auditory canal, the support bar moves into the hanndle.

5. The earpick of claim 4, wherein a portion of the support bar pressed by the concave grooves has a plurality of concave-convex portions.

6. The earpick of claim 1, wherein one end of the support bar is flat, so that when the support bar is pulled out, the flat end prevents the support bar from being separated from the handle.

7. An earpick, comprising:

a handle;

a support bar movably coupled to the handle;

an earwax cleaning portion coupled to the support bar; and an elastic plate folded in a laid letter "U" form, the elastic plate having a through hole and concave grooves opposite to each other, wherein the support bar passes through the through hole and is pressed by the concave grooves, the earwax cleaning portion has a ring shaped cross-section, and when the earpick deeply enters and contacts an inner wall of an auditory canal, the support bar moves into the hanndle.

8. The earpick of claim 7, wherein a portion of the support bar pressed by the concave grooves has a plurality of concave-convex portions.

9. An earpick, comprising:

a handle;

a support bar movably coupled to the handle; and an earwax cleaning portion coupled to the support bar, wherein the handle includes a front handle and a rear handle screw-coupled to each other, and when the earpick deeply enters and contacts an inner wall of an auditory canal, the support bar moves into the hanndle.

10. The earpick of claim 9, wherein the rear handle has at least one flat portion formed in the same direction of the earwax cleaning portion.

* * * * *

UNITED STATES PATENT AND TRADEMARK OFFICE
CERTIFICATE OF CORRECTION

PATENT NO. : 6,776,786 B2  
DATED : August 17, 2004  
INVENTOR(S) : Y. Kim

It is certified that error appears in the above-identified patent and that said Letters Patent is hereby corrected as shown below:

Column 3,
Line 26, after "bar;" insert -- and --.

Column 4,
Lines 4 and 28, "hanndle" should be -- handle --.

Signed and Sealed this

Fifth Day of April, 2005

JON W. DUDAS
*Director of the United States Patent and Trademark Office*